United States Patent
Everett et al.

(10) Patent No.: US 12,097,226 B2
(45) Date of Patent: *Sep. 24, 2024

(54) SYSTEM AND METHOD FOR USING A SINGLE-SERVE NUTRIENT SPORE COMPOSITION FOR SMALL SCALE FARM APPLICATIONS

(71) Applicant: NCH Corporation, Irving, TX (US)

(72) Inventors: Gabby Everett, Mansfield, TX (US); Charles Greenwald, Irving, TX (US); Jordan E. Church, Carrollton, TX (US); Lester Levy, Dallas, TX (US); Nicole Faris, Flower Mound, TX (US); Joshua Medford, Grand Prairie, TX (US)

(73) Assignee: NCH Corporation

( * ) Notice: Subject to any disclaimer, the term of this patent is extended or adjusted under 35 U.S.C. 154(b) by 392 days.

This patent is subject to a terminal disclaimer.

(21) Appl. No.: 17/207,932

(22) Filed: Mar. 22, 2021

(65) Prior Publication Data

US 2021/0205377 A1 Jul. 8, 2021

Related U.S. Application Data

(60) Continuation-in-part of application No. 16/785,138, filed on Feb. 7, 2020, now Pat. No. 11,484,556, which is a division of application No. 15/479,773, filed on Apr. 5, 2017, now Pat. No. 10,610,552.

(60) Provisional application No. 62/993,406, filed on Mar. 23, 2020, provisional application No. 62/318,587, filed on Apr. 5, 2016.

(51) Int. Cl.

| | |
|---|---|
| A61K 35/742 | (2015.01) |
| A23L 29/00 | (2016.01) |
| A61K 47/02 | (2006.01) |
| C02F 3/34 | (2023.01) |
| C12N 1/04 | (2006.01) |
| C12N 1/20 | (2006.01) |
| C12N 3/00 | (2006.01) |
| C12R 1/01 | (2006.01) |
| C12R 1/07 | (2006.01) |
| C12R 1/125 | (2006.01) |

(52) U.S. Cl.
CPC .......... *A61K 35/742* (2013.01); *A23L 29/065* (2016.08); *A61K 47/02* (2013.01); *C02F 3/34* (2013.01); *C02F 3/348* (2013.01); *C12N 1/04* (2013.01); *C12N 1/20* (2013.01); *C12N 1/205* (2021.05); *C12N 3/00* (2013.01); *C12R 2001/01* (2021.05); *C12R 2001/07* (2021.05); *C12R 2001/125* (2021.05)

(58) Field of Classification Search
None
See application file for complete search history.

(56) References Cited

U.S. PATENT DOCUMENTS

| | | |
|---|---|---|
| 5,501,857 A | 3/1996 | Zimmer |
| 6,051,219 A | 4/2000 | Kubota |
| 6,327,965 B1 | 12/2001 | Tien |
| 6,335,191 B1 | 1/2002 | Kiplinger et al. |
| 6,461,607 B1 | 10/2002 | Farmer |
| 6,849,256 B1 | 2/2005 | Farmer |
| 7,081,361 B2 | 7/2006 | Pearce, III et al. |
| 7,635,587 B2 | 12/2009 | Pearce, III et al. |
| 7,713,726 B2 | 5/2010 | Farmer |
| 7,736,509 B2 | 6/2010 | Kruse |
| 7,754,469 B2 | 7/2010 | Baltzley et al. |
| 8,093,040 B2 | 1/2012 | Pearce, III et al. |
| 8,192,733 B2 | 6/2012 | Cobb et al. |
| 8,277,799 B2 | 10/2012 | Farmer |
| 8,349,337 B1 | 1/2013 | Farmer et al. |
| 8,506,951 B2 | 8/2013 | Rehberger et al. |
| 8,540,981 B1 | 9/2013 | Wehnes et al. |
| 8,551,762 B2 | 10/2013 | Fleming et al. |
| 8,647,690 B2 | 2/2014 | Corrigan |
| 8,822,208 B2 | 9/2014 | Chokshi |
| 9,011,834 B1 | 4/2015 | McKenzie et al. |

(Continued)

FOREIGN PATENT DOCUMENTS

| | | |
|---|---|---|
| CA | 2778144 | 5/2011 |
| CN | 1528681 | 9/2004 |

(Continued)

OTHER PUBLICATIONS

Marinova et al. Biotechnology and Biotechnological Equipment, 22:,835-838, 2008.*
A. Aland and T. Banhazi (eds.) (Hereinafter "Aland et al") Livestock housing: modern management to ensure optimal health and welfare of farm animals DOI 10.3920/978-90-8686-771-4_07, © Wageningen Academic Publishers 2013, pp. 147-159.*
Janne Hansen. Pigs drink both day and night. Jun. 20, 2012. Retrieved on Sep. 12, 2023 from https://anivet.au.dk/en/current-news/news/show/artikel/translate-to-english-soeer-drikker-dag-og-nat.*

(Continued)

*Primary Examiner* — Oluwatosin A Ogunbiyi
(74) *Attorney, Agent, or Firm* — Scheef & Stone, LLP; Robin L. Barnes

(57) ABSTRACT

A system and method for incubating a nutrient spore composition to at least begin the germination process at a point-of-use for small-scale farm applications. The composition comprises solid or powdered L-amino acids, a buffer, optionally D-glucose and/or D-fructose, optionally potassium, and *Bacillus* spores in a pre-measured filter packet. The method comprises adding a small amount of hot water in a temperature range of 60° C. to 80° C. to the filter packet for an incubation period of around 2 to 60 minutes to form an incubated bacteria solution that is discharged to a farm application. A drip-style coffee maker or similar system may be used to add hot water to the filter packet. The incubated bacteria solution is dispensed to animal drinking water, plants/crops, or an aquaculture pond.

25 Claims, 1 Drawing Sheet

(56) References Cited

U.S. PATENT DOCUMENTS

| | | |
|---|---|---|
| 9,447,376 B2 | 9/2016 | Hashman et al. |
| 9,932,543 B2 | 4/2018 | Hashman et al. |
| 10,766,799 B2 | 9/2020 | Greenwald et al. |
| 10,897,922 B2 | 1/2021 | Church et al. |
| 2003/0165472 A1 | 9/2003 | McGrath et al. |
| 2003/0228679 A1 | 12/2003 | Smith et al. |
| 2004/0232069 A1 | 11/2004 | Shaffer |
| 2005/0255092 A1 | 11/2005 | Rehberger et al. |
| 2008/0241226 A1 | 10/2008 | Abeln et al. |
| 2009/0186057 A1 | 7/2009 | Farmer et al. |
| 2009/0232941 A1 | 9/2009 | Farmer |
| 2009/0242173 A1 | 10/2009 | Mitchell |
| 2010/0124586 A1 | 5/2010 | Becker |
| 2011/0230345 A1 | 9/2011 | Snyder et al. |
| 2011/0256216 A1 | 10/2011 | Lefkowitz |
| 2012/0034344 A1 | 2/2012 | Menon |
| 2012/0052152 A1 | 3/2012 | Armentrout |
| 2012/0100094 A1 | 4/2012 | Reuter et al. |
| 2012/0296075 A1 | 11/2012 | Reed et al. |
| 2013/0092087 A1 | 4/2013 | Bachman et al. |
| 2013/0171204 A1 | 7/2013 | DuBourdieu |
| 2014/0295482 A1 | 10/2014 | Lyte |
| 2015/0079661 A1 | 3/2015 | Pruitt |
| 2015/0299636 A1 | 10/2015 | Virtanen et al. |
| 2015/0336828 A1 | 11/2015 | Greenwald et al. |
| 2016/0113289 A1 | 4/2016 | Patel et al. |
| 2017/0042949 A1 | 2/2017 | Penaloza-Vazquez |
| 2017/0087199 A1 | 3/2017 | Patron |
| 2017/0175070 A1 | 6/2017 | Boyette et al. |
| 2017/0246222 A1 | 8/2017 | Lewis |
| 2017/0281696 A1 | 10/2017 | Everett et al. |
| 2019/0071336 A1 | 3/2019 | Greenwald et al. |
| 2019/0098915 A1 | 4/2019 | Church et al. |
| 2019/0100723 A1 | 4/2019 | Church et al. |
| 2020/0078751 A1 | 3/2020 | Schuster et al. |
| 2020/0071661 A1 | 5/2020 | Greenwald et al. |

FOREIGN PATENT DOCUMENTS

| | | | | |
|---|---|---|---|---|
| CN | 104312954 A | * | 1/2015 | |
| CN | 102387703 | | 3/2021 | |
| JP | 5724217 | | 5/2015 | |
| KR | 100865682 | | 10/2008 | |
| WO | WO-9905310 A1 | * | 2/1999 | ............... C12Q 1/22 |
| WO | WO1999005310 | | 2/1999 | |
| WO | WO-0010582 A2 | * | 3/2000 | ............. A61K 31/43 |
| WO | WO2004024865 | | 3/2004 | |
| WO | WO-2009051753 A1 | * | 4/2009 | ............... A23F 3/14 |
| WO | WO2009126473 | | 10/2009 | |
| WO | WO2010045541 | | 4/2010 | |
| WO | WO2010066012 | | 6/2010 | |
| WO | WO2012079973 | | 6/2012 | |
| WO | WO2013119493 | | 8/2013 | |
| WO | WO2013142792 | | 9/2013 | |
| WO | WO2014193746 | | 12/2014 | |
| WO | WO-2014193746 A1 | * | 12/2014 | ............. A01N 63/00 |
| WO | WO2015038892 | | 3/2015 | |
| WO | WO2016044661 | | 3/2016 | |
| WO | WO2017117089 | | 7/2017 | |
| WO | WO2019090065 | | 5/2019 | |
| WO | WO2019168627 | | 9/2019 | |
| WO | WO2019222168 | | 11/2019 | |
| WO | WO2020212384 | | 10/2020 | |

OTHER PUBLICATIONS

The Tea Table. "How Big is a Tea Cup?" https://www.theteatable.com/blog/how-big-is-a-tea-cup Jul. 28, 2009.*

Billow et al. "Steep Your Way to Hot Tea Perfection by Avoiding These Common Mistakes" retrieved from https://www.bonappetit.com/test-kitchen/common-mistakes/article/hot-tea-common-mistakes retrieved on Mar. 1, 2024.*

American Society of Agronomy (ASA), Crop Science Society of America (CSSA). "Probiotics—for plants." ScienceDaily ScienceDaily, Jul. 8, 2015 Jul. 8, 2015.

Balcazar et al., The role of probiotics in aquaculture, Veterinary microbiology 114.3, 173-186, 2006 Jan. 17, 2006.

Bentzon-Tilia et al., Monitoring and Managing Microbes in Aquaculture-Towards a sustainable industry, MIcrobial biotechnology 9.5, 576-584, 2016 Apr. 24, 2016.

Farzanfar, The use of probiotics in shrimp aquaculture, FEMS Immunology & Medical Microbiology 48.2, 149-158, 2006 Apr. 20, 2006.

Furtado et al., Effect of calcium hydroxide, carbonate and sodium bicarbonate on water quality and zootechnical performance of shrimp Litopenaeus vannamei reared in bio-flocs technology (BFT) systems, Aquaculture 321.1, 130-135, 2011 Sep. 8, 2011.

Hai, The use of probiotics in aquaculture, Journal of applied microbiology 119.4, 917-935, 2015 Jun. 22, 2015.

Joint FAO/WHO Expert Consultation on Evaluation of health and nutritional properties of probiotics in food including powder milk with live lactic acid bacteria, Cordoba, Argentina. Oct. 1-4, 2001 Oct. 1, 2001.

Kumar et al, Bacillus as PGPR in crop ecosystem; Bacteria in agrobiology: crop ecosystems. Springer Berlin Heidelberg, 37-59, 2011 2011.

Lakshmi et al., Probiotics as antiviral agents in shrimp aquaculture, Journal of pathogens 2013 Apr. 9, 2013.

Mahdhi et al., Survival and retention of the probiotic properties of *Baccilus* sp. strains under marine stress starvation conditions and their potential use as a probiotic in Artemia culture, Research in veterinary science 93.3, 1151-1159, 2012 Dec. 2012.

Sahu et al., Probiotics in aquaculture: importance and future perspectives. Indian journal of microbiology 48.3, 299-308 2008 Jun. 13, 2008.

Busta, F.F. and Ordal, Z.J., Use of Calcium Dipicolinate for Enumeration of Total Viable Endospore Populations without Heat Activation, Applied Microbiology, Mar. 1964, p. 106-110, vol. 12, No. 2, American Society for Microbiology.

Carrillo-Martinez, Yarery and Setlow, Peter, Properties of Bacillus subtilis Small, Acid-Soluble Spore Proteins with Changes in the Sequence Recognized by Their Specific Protease, Journal of Bacteriology, Sep. 1994, p. 5357-5363, vol. 176, No. 17, American Society for Microbiology.

Kleijn, Roelco; Buescher, Joerg M.; Le Chat, Ludovic; Jules, Matthieu; Aymerich, Stephane; and Sauer, Uwe, Metabolic Fluxes during Strong Carbon Catabolite Repression by Malate in Bacillus subtilis, Journal of Biological Chemistry, Jan. 15, 2010, p. 1587-1596, vol. 285, No. 3, The American Society for Biochemistry and Molecular Biology, Inc.

Kong, Lingbo; Zhang, Pengfei; Wang, Guiwen; Yu, Jing; Setlow, Peter; and Li, Yong-Qing, Charactization of bacterial spore germination using phase-contrast and fluorescence microscopy, Raman spectroscopy and optical tweezers, Nature Protocols, Mar. 2011, p. 625-639, vol. 6, No. 5.

Madslien, Elisabeth H.; Granum, Per Einar; Blatny, Janet M; and Lindback, Toril, L-alanine-induced germination in Bacillus licheniformis—the impact of native gerA sequences, BMC Microbiology, published 2014, p. 1-10.

Martin, J. H. and Harper, W. J., Germination Response of Bacillus Licheniformis Spores to Amino Acids, Department of Dairy Technology, Journal of Dairy Science, Jul. 1963, p. 663-667.

Segev, Einat; Rosenberg, Alex; Mamou, Gideon; Sinai, Lior; and Ben-Yehuda, Sigal, Molecular Kinetics of Reviving Bacterial Spores, Journal of Bacteriology, May 2013, p. 1875-1882, vol. 195, No. 9.

Setlow, Peter, Summer Meeting 2013—when the sleepers wake: the germination of spores of *Bacillus* species, Journal of Applied Microbiology, Sep. 2013, p. 1251-1268.

Sinai, Lior; Rosenberg, Alex; Smith, Yoav; Segev, Einat; and Ben-Yehuda, Sigal, The Molecular Timeline of a Reviving Bacterial Spore, Molecular Cell, Feb. 2015, p. 695-707.

Yi, Xuan and Setlow, Peter, Studies of the Commitment Step in the Germination of Spores of *Bacillus* Species, Journal of Bacteriology, Jul. 2010, p. 3424-3433, vol. 192, No. 13.

(56) References Cited

OTHER PUBLICATIONS

Zhang, Pengfei; Setlow, Peter; and Li, Yongqing, Characterization of single heat-activated Bacillus spores using laser tweezers Raman spectroscopy, Optics Express, Sep. 2009, p. 16480-16491, vol. 17, No. 19.
Curran et al., Heat Activation Inducing Germination in the Spores of Thermotolerant and Thermophilic Aerobic Bacteria, Journal of Bacteriology; Apr. 1945; vol. 49, No. 4, pp. 335-346.
Sigmaaldrich.com, Buffer Reference Center, Webpage [online]; Apr. 30, 2015 [date verified by web.archive.org; retrieved on Jun. 2, 2017]. Retrieved from the Internet: URL: www.sigmaaldrich.com/ life-science/core-bioreagents/biological-buffers/learning-center/buffer-reference-center.
Stewart et al., Commitment of bacterial spores to germinate: A measure of the trigger reaction. Biochemical Journal. Jul. 15, 1981, vol. 198, No. 1; pp. 101-106.
Boukarim et al., Preservatives in Liquid Pharmaceutical Preparations; The Journal of Applied Research; published 2009 (month unknown); vol. 9, No. 1-2; pp. 14-17.
Nagler, et al., High Salinity Alters the Germination Behavior of Bacillus subtilis Spores with Nutrient and Nonnutrient Germinants. Applied and Environmental Microbiology. Feb. 2014, vol. 80, No. 4; pp. 1314-1321.
Yasuda, Yoko and Tochikubo, Kunio, Relation between D-Glucose and L-and D-Alanine in the Initiation of Germination of Bacillus subtilis Spore, Microbio. Immunol. Oct. 1983, p. 197-207, vol. 28. No. 2.
Cutting, Simon M., Bacillus Probiotics, Food Microbiology, 2011, vol. 28, pp. 214-220.
Chedia, Aquadhi et al., Optimization of nutrient-induced germination of Bacillus sporothermodurans spores using response surface methodology, Food Microbiology, Academic Press Ltd, V. 36, N. 2, Jul. 8, 2013, pp. 320-326.
Ramirez-Peralta, Arturo et al, Effects of 1-16 sporulation conditions on the germination and germination protein levels of Bacillus subtilis spores, Applied and Environmental Microbiology Apr. 2012, V. 78, N. Apr. 8, 2012, pp. 2689-2697.
Wang, Shiwei et al, Slow Leakage of Ca-Dipicolinic Acid from Individual Bacillus Spores during Initiation of Spore Germination, Journal of Bacteriology, V. 197, N. 6, Mar. 2015, pp. 1095-1103.
Luu, Stephanie, et al., The Effects of Heat 1-16 Activation on Bacillus Spore Germination, with Nutrients or under High Pressure, with or without Various Germination Proteins, Applied and Environmental Microbiology, V. 81, N. 8, Feb. 13, 2015, pp. 2927-2398.
Timmermann et al., Metabolism and Nutrition Mortality and Growth Performance of Broilers Given Drinking Water Supplemented with Chicken-Specific Probiotics, Poultry Science, vol. 85, Aug. 1, 2006, pp. 1383-1388.
Katsutoshi et al., Effect of spore-bearing lactic acid-forming bacteria (Bacillus coagulans SANK 70258) administration on the intestinal environment, defecation frequency, fecal characteristics and dermal characteristics in humans and rats, Microbial Ecology in Health & Dis, Co-Action Publishing, SE, vol. 14, No. 1, Mar. 2002, pp. 4-13.
Casula, G and S. Cutting. 2002. Bacillus Probiotics: Spore Germination in the Gastrointestinal Tract. American Society for Microbiology. vol. 68, No. 5: 2344-2352.
Wikipedia, "Sodium chloride", Nov. 1, 2017, retrieved on Apr. 5, 2019 from https://en.wikipedia.org/w/index.php?title=Sodium_chloride&oldid=808219406, pp. 1-9.
Gurung, Neelam, et al., A Broader View: Microbial Enzymes and Their Relevance in Industries, Medicine, and Beyond, BioMed Research International; vol. 2013, Article ID 329121.
Yazdi, Mohammed A., et al., Characterization and cloning of the gerC locus of Bacillus subtilis 168, Journal of General Microbiology, 1990, 136, 1335-1342.
EcoBionics Biological System Data Sheet, believed to be published at least as early as 2016 (relates to Bioamp).
Nguyen, Bacillus subtilis spores expressing the VP28 antigen; a potential oral treatment to protect Litopenaeus vannamei against white spot syndrome, FEMS Microbiilogy Letters 01, Sep. 2014 (Sep. 1, 2014), vol. 358, pp. 202-208, p. 203.
Waites, The Effect of pH, Germinants and Temperature on the Germination of Spores of Clostridium bifermentans, Journal of General Microbiology, 1974, 80, 253-258 (Year: 1974).
Shearer et al., Bacterial Spore Inhibition and Inactivation in Foods by Pressure, Chemical Preservatives, and Mild Heat, Journal of Food Protection, Nov. 2000, vol. 63, pp. 1503-1510, p. 1504-1505.
Setlow, Germination of Spores of Bacillus Species, What We Know and Do Not Know, Journal of Bacteriologoy, Apr. 2014, vol. 196, pp. 1297-1305, p. 1298.
Soni et al., Safety Assessment of Propyl Paraben: a review of the published literature, Food and Chemical Toxicology vol. 39, 2001, p. 513-532.
Mohan, Chandra, A guide for the preparation and use of buffers in biological systems, CalBiochem Buffers, 2003; http://www.antibodybeyond.com/books/Calbiochem_Buffers_Booklet_CB0052_E.pdf, retrieved Mar. 8, 2020.
Wax, R. et al. Separation of Two Functional Roles of L-Alanine in the Initiation of Bacillus subtilis Spore Generation. J of Bacteriology 94(3)522-529, Sep. 1967 (Year: 1967).
Wuytack, E. et al. Comparative Study of Pressure and Nutrient Induced Germination of Bacillus subtilis Spores. Applied and Environmental Microbiology 66(1)257-261, Jan. 2000. (Year: 2000).
Bergeys Manual of Systematics Archaea and Bacteria, John Wiley & Sons, Bacillus chapter 1-164, 2015 (Year: 2015).
Mitsuhashi T "Effects of and L-alanine on the Swelling of Bacillus subtilis spores during germination"—Nippon suisan Gakkaishi—Bulletin of Japanese Society of Scientifici Fisheries, vol. 59, No. 5 1993 pp. 841-846.
Bader J "Spore-forming bacteria and their utilisation as probiotics" Beneficial Microbes, vol. 3, No. 1, Mar. 1, 2012 pp. 67-75.
Safe Feeding with Lupro-Grain and Amasil NA—product brochure available from BASF Chemical Company, published at least as early as 2011, Retrieved. from the Internet on Feb. 16, 2015 at <URL: http://www.basfanimalnutrition.de/downloads/an_safe_feeding_en.pdf and http://www.basfanimalnutrition.de/en/news_2008_09_09.php>.
Supporting More Sustainable Livestock Production Luprosil & Amasil Less Spoilage, Improved Hygiene, product brochure from BASF Chemical Company, believed published at least as early as 2011, Retrieved from the Internet on Feb. 16, 2015 at <URL: http://www.newtrition.basf.com/web/global/de/function/conversions:/publish/content/microsites/animal-nutrition/Sustainability_Contribution/assets/Luprosil_Amasil. pdf>.
Bactocell Drink on-tracks for EU authorization as a feed additive for use in drinking water for swine and poultry, news release from Lallemand Animal Nutrition, published Aug. 29, 2012, Retrieved from the Internet on Feb. 16, 2016 at <URL: http ://1 al lerna nda n i rn a In utritio n. corn/ news/bactocel 1-d rink-a n-tracks-fo r-eu-a uthorizati on- as-a-feed- additive-for -use-i n-d rinking-water -for-swine-and-poultry/>.
Poultry Product Quality—product information regarding BioPlus available from Chr. Hansen, believed to be published at least as early as 2011, Retrieved from the Internet on Feb. 16, 2016 at <URL: http://www.chr-hansen.com/animal-probiotics-and-silage-inoculants/probiotics-for-poultry/poultry-product-quality>.
European Food Safety Authority Scientific Opinion on the Safety and Efficacy of BioPlus 2B, published in the EFSA Journal 2011; 9(9):2356, Retrieved from the Internet on Feb. 16, 2016 at <URL: http://www.efsa.europa.eu/sites/default/files/scientific_output/files/main_documents/2356.pdf>.
European Food Safety Authority Scientific Opinion on the Safety and Efficacy of Bactocell, published in the EFSA Journal 2012; 10(7):2776, Retrieved from the Internet on Feb. 16, 2016 at <URL: http://www.efsa.europa.eu/sites/default/files/scientific_output/files/main_documents/2776.pdf>.
Biotic for Shrimp—product information available from Biopharmachemie, believed to be published at least as early as 2011, Retrieved from the Internet on Feb. 16, 2016 at <URL: http://biopharmachemie.com/product/products-for-shrimp/biotic-for-shrimp.html>.

(56) References Cited

OTHER PUBLICATIONS

Biozyme for Shrimp—product information available from Biopharmachemie, believed to be published at least as early as 2011, Retrieved from the Internet on Feb. 16, 2016 at <URL: http://biopharmachemie.com/product/products-for-shrimp/biozyme-for-shrimp.html>.

Biotic for Poultry and Swine—product information available from Biopharmachemie, believed to be published at least as early as 2011, Retrieved from the Internet on Feb. 16, 2016 at <URL: http://www.biopharmachemie.com/product/products-for-livestock/biotic.html>.

Delivering superior swine performance—product information on VevoVitall available from DSM, believed to be published at least as early as 2011, Retrieved from the Internet on Feb. 16, 2016 at <URL: http://www.dsm.com/marketslanh/en_US/products/products-eubiotics/products-eubiotics-vevovitall.html>.

Selko-pH Health Promoter water, Three Steps to Improve intestinal health via drinking water, product information available from Seiko, believed to be published at least as early as 2011, Retrieved from the Internet on Feb. 16, 2016 at <URL: http://www.amcra.be/sites/default/files1Jaco%20Eisen%20Selko%20Feed%20Additives.pdf>.

Selko-Ph, product information available from Seiko, believed to be published at least as early as 2011, Retrieved from the Internet on Feb. 16, 2016 at <URL: http://www.selko.com/en/products/selko-ph/9129>.

FloraMax B-11, (Tech Sheet) product information available from Ivesco, believed to be published at least as early as 2011 (product available since 2004), Retrieved from the Internet on Feb. 16, 2016 at <URL: http://www.ivescopoultry.com/Attachment/5/20535_5_FloraMaxTechSheet.pdf>.

FloraMax B-11 Proven in the lab . . . confirmed in the field, product information available from Pacific Vet Group, believed to be published at least as early as 2011 (product available since 2004), Retrieved from the Internet on Feb. 16, 2016 at <URL: http://www.pacificVetgroup.com/docs/PVG-FloraMaxB-11.pdf>.

Fortify Liquid Concentrated Direct-Fed Microbial for Drinking Water, product label available from Assist Natural Products and Services, LLC, believed to be published at least as early as 2013, Retrieved from the Internet on Feb. 16, 2016 at <URL: http://www.assist-nps.com/files/Fortify%20Liquid%20Label.pdf>.

Calsporin, product information available from Calpis Co., Ltd., 4-1, Ebisu-Minami 2-chome Shibuya, Tokyo, Japan, believed to be published at least as early as 2013 (product available since at least 2000).

Calsporin Swine FAQ, product information available from Quality Technology International, Inc., published 2012, Retrieved from the Internet on Feb. 16, 2016 at <URL: http://www.qtitechnology.com/sites/default/files/pdfs/CalsporinSwineFAQ.pdf>.

Calsporin Poultry FAQ, product information available from Quality Technology International, Inc., published 2012, Retrieved from the Internet on Feb. 16, 2016 at <URL: http://www.qtitechnology.com/sites/default/files/pdfs/CalsporinPoultryFAQ.pdf>.

Proflora Live DFM: Bacillus Subtilis Strain QST 713, product information available from Zoetis, 100 Campus Drive, Florham Park, New Jersey 07932, believed to be published at least as early as 2013.

Proflora Live DFM: Bacillus Subtilis Strain QST 713, product information available from Zoetis, believed to be published at least as early as 2013, Retrieved from the Internet on Feb. 16, 2016 at <URL: https://www.zoetisus.com/ products/ poultry lp rofto ra. as px>.

BioGrow & Provita Gameguard, product information available from Provita Eurotech Limited, 21 Bankmore Road, Omagh, County Tyrone, Northern Ireland, believed to be published at least as early as 2013 (BioGrow product available since 2001).

Biogrow, product information available from Provita, believed to be published at least as early as 2013 (BioGrow product available since 2001), Retrieved from the Internet on Feb. 16, 2016 at <URL: http://www.provita.co.uk/poultry/biogrow>.

Swine Bluelite 2Bw a water soluble acidified electrolyte product with probiotics for pigs, product information available from TechMix Global, published Sep. 2011, Retrieved from the Internet on Feb. 16, 2016 at <URL: https://web.archive.org/web/20110909124607/http://www.techmixglobal.com/swine-bluelite-2bw>.

Chorawala, M. R., P. M. Oza, G. B. Shah. 2011. Probiotics, Prebiotics and Synbiotics: A Health Benefit Supplement. Research Journal of Pharmaceutical, Biological and Chemical Sciences vol. 2 (3): 1101-1111.

Patterson, J.A., K. M. Burkholder. 2003. Application of prebiotics and probiotics in poultry production. Poultry Science 82:627-631.

ADM Animal Nutrition, Direct Fed Microbial: Application and Usage Data Sheet, retrieved on Jan. 16, 2017 from http://www.admani.com/animalhealth/techbulletins/animaldirect.

Amerah, A.M., C. J. van Rensburg, P. W. Plumstead, C. Kromm, and S. Dunham. 2013. Effect of feeding diets containing a probiotic or antibiotic on broiler performance, intestinal mucosa-associated avian pathogenic E. coli and litter water-soluble phosphorus. Journal of Applied Animal Nutrition, vol. 1; E 7.

Sutton, A. L., K. B. Kephart, M. W. A. Verstegen, T. T. Canh, and P. J. Hobbs. Potential for reduction of odorous compounds in swine manure through diet modification. Journal of Animal Science, 1999, 77:430-439.

Davis, M. E., T. Parrott, D. C. Brown, B. Z. de Rodas, Z. B. Johnson, C. V. Maxwell, T. Rehberger. 2008. Effect of a Bacillus-based direct-fed microbial feed supplement on growth performance and pen cleaning characteristics of growing-finishing pigs. Journal of Animal Science, 2008, 86:1459-1467.

Bactocell Drink is Now Authorized in Europe as a Feed Additive for Swine and Poultry, news release from Lallemand Animal Nutrition, published May 15, 2013, Retrieved from the Internet on Feb. 16, 2016 at <URL: http://lallemandanimalnutrition.com/news/bactocell-drink-is-now-authorized-in-europe-as-a-feed-additive-for-swine-and-poultry/>.

Activate & Activate WD Max Product Information available from Nevus, believed published at least as early as 2011, Retrieved from the Internet on Feb. 16, 2016 at http://novusintqa.enlivenhq.com/Products/activate#fndtn-activatewdmax.

\* cited by examiner

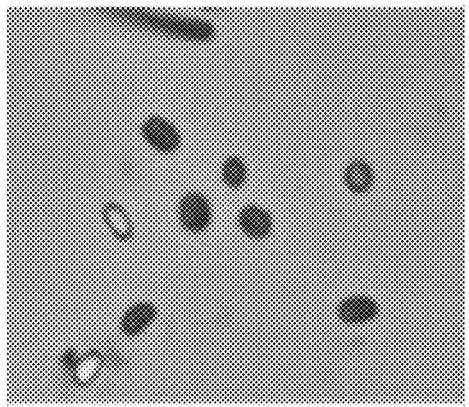
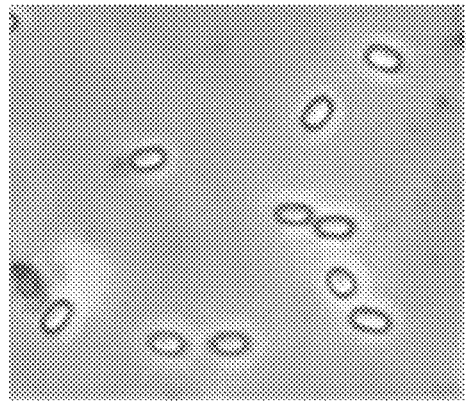
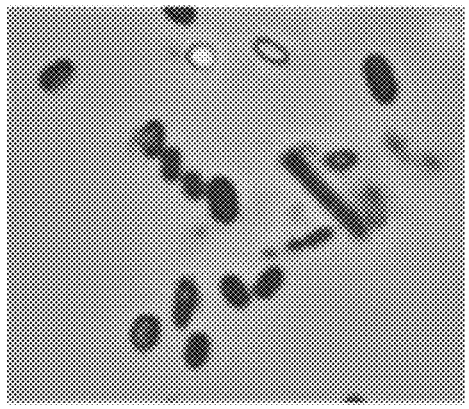
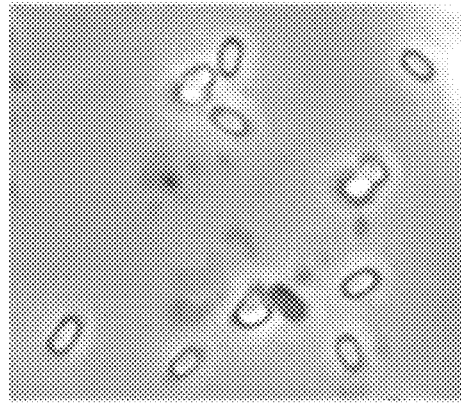
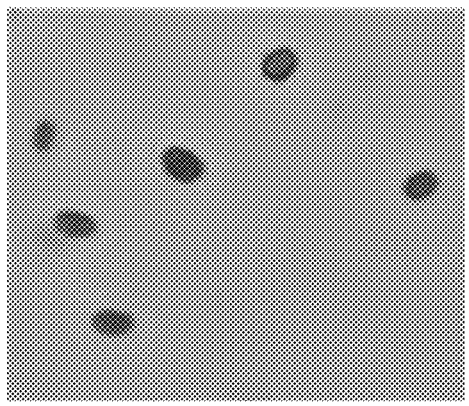
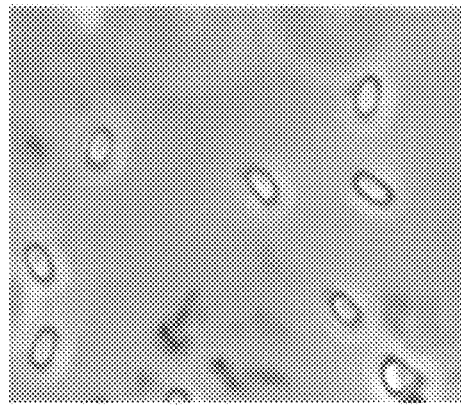
Panel A
Panel B

SYSTEM AND METHOD FOR USING A SINGLE-SERVE NUTRIENT SPORE COMPOSITION FOR SMALL SCALE FARM APPLICATIONS

CROSS-REFERENCE TO RELATED APPLICATION

This application claims the benefit of U.S. Provisional Application Ser. No. 62/993,406 filed on Mar. 23, 2020. This application is also a continuation-in-part of U.S. application Ser. No. 16/785,138 filed on Feb. 7, 2020, now U.S. Pat. No. 11,484,556, which is a divisional of U.S. Ser. No. 15/479,773 filed on Apr. 5, 2017, now U.S. Pat. No. 10,610,552, which claims the benefit of U.S. provisional patent application No. 62/318,587 filed Apr. 5, 2016.

BACKGROUND OF THE INVENTION

1. Field of the Invention

This invention relates to systems and methods for incubating a single-serve amount of nutrient spore composition comprising *Bacillus* spores using a point-of-use spore rehydration and heating method for small scale farm applications, such as application to animal drinking water to improve animal gut health.

2. Description of Related Art

Gut health plays an integral role in the overall well-being of animals. The gut of all animals is inhabited by bacteria, also known as the microbiome or microbiota. Gastrointestinal functionality, the steady state in which the microbiome and the intestinal tract exist in symbiotic equilibrium, is essential for proper nutrient absorption. When there is a microbiota imbalance, many animals experience malabsorption, a higher instance of pathogenic diseases, stress, and many other issues.

It is estimated that 70% of the immune response resides in the gut, as the gut tends to be the first line of defense against pathogens. A common route of entry for various pathogens (*Salmonella, Escherichia coli*, etc.) is orally. When these pathogens reach the gut, they encounter the microbiome which acts as a physical barrier to colonization. In addition, proper gut health increases the length of the intestinal villi, the finger-like projections in the intestine responsible for nutrient absorption. Long villi create another physical barrier that inhibits harmful pathogens and toxins. Improper nutrient absorption causes gaps in the tight junctions in between the cells of the intestinal wall which allows bacteria and other toxins to pass through into the bloodstream. This condition, known as Leaky Gut Syndrome, is a common disease in all animal species and one prevalent in the agricultural and aquaculture industries. Proper nutrient absorption and an increase in healthy gut bacteria may reduce the incidence of Leaky Gut Syndrome by improving villi structure.

Probiotics are live microorganisms that provide health benefits when consumed in adequate amounts. Studies conducted with probiotics have shown a reduced incidence of pathogenic diseases, decreased stress, prevention and treatment of diarrhea, immune system support, and the balancing of bacteria in the digestive system.

Probiotics are not limited to animals—they also provide benefits to plants. Plants treated with plant growth-promoting probiotic bacteria, like *Bacillus*, show increased nutrient absorption. An added benefit of probiotics is that they inhibit root colonization by pathogenic bacteria, and provide enhanced resistance to disease.

In general, there are two types of probiotics: live, active probiotics and *Bacillus*-based probiotics which are composed of spores. A spore is a natural, dehydrated, dormant state that is distinctive to specific species of bacteria and confers certain resistances (e.g. heat, starvation, pH, etc.). Live, active probiotics, including yogurt, use bacterial species including *Bifidobacterium* and *Lactobacillus*. These species do not have a dormant state, so when fed to animals, they enter the stomach alive and vulnerable. Many of the cells do not survive the acidic conditions in the stomach and therefore, may have a reduced impact on gut health.

*Bacillus*-based probiotics are formulated as spores and are resistant to stomach acid because of their protective coat. When fed to animals, spores survive stomach acid; however, most do not activate and remain dormant when they reach the intestine resulting in reduced impact on gut health. Spore activation in the small intestine is important because this is where most nutrient absorption and immune system development takes place. There is a need for a system and method for rapid activation of *Bacillus*-based probiotics in a single step and without requiring a separate heat activation step so that the germination process can begin before the bacteria reach the small intestine to allow the bacteria to become live, active bacteria while in the small intestine.

Spore germination is a multistep, causative process wherein spores effectively wake-up or are revived from a dormant state to a vegetative growth state. The first step is one by which spores are activated and are induced to germinate, typically by an environmental signal called a germinant. This signal can be a nutrient such as an L-amino acid. Nutrient-germinants bind to receptors in the inner-membrane of the spore to initiate germination. Additionally, sugars have been shown to increase the binding affinity of L-amino acids for their cognate receptors.

The germinant signal initiates a cascade that causes the release of Dipicolinic Acid (DPA), which is stored in a 1:1 ratio with $Ca^{2+}$ (CaDPA) in the core of the spore. The release of CaDPA is a fast process and is typically >90% complete in 2 min. CaDPA release represents a point of no return for spores in which they are committed to the germination process. This is known in the art as the "commitment" step.

After CaDPA release, the spore is partially hydrated and the core pH rises to approx. 8.0. The core of the spore then expands and the cortex (composed mostly of peptidoglycan) is degraded by core lytic enzymes. The spore absorbs water and consequently loses its refractivity. This loss of refractivity towards the end of the germination process allows spore germination to be monitored via phase-contrast microscopy.

The second phase of germination is an outgrowth step in which the spore's metabolic, biosynthetic, and DNA replication/repair pathways initiate. The outgrowth period has several phases. The first is known as a ripening period in which no morphological changes (such as cell growth) occur, but the spore's molecular machinery (e.g. transcription factors, translation machinery, biosynthesis machinery, etc.) is activated. This period can vary in length based on the initial resources that are packaged with the spore during the process of sporulation. For instance, the preferred carbon source of several *Bacillus* species (including *subtilis*) is malate and *Bacillus* spores typically contain a large pool of malate that is used during the revival process. Interestingly, deletion mutants that cannot utilize the malate pool display an extended ripening period compared to wild-type spores indicating that the spore malate pool is sufficient to energize the initial outgrowth process. Additionally, spores store small, acid-soluble proteins that are degraded within the first several minutes of revival that serve as an immediate source of amino acids for protein synthesis. After the outgrowth step, spore revival is complete and cells are considered to be vegetatively growing.

It is known that spores can be induced to germinate via heat-activation. Spores of various *Bacillus* species have been heat-activated at strain-specific temperatures. For example, *B. subtilis* spores have been heat-activated at 75° C. for 30 minutes while *B. licheniformis* spores have been heat-activated at 65° C. for 20 minutes. The heat-activation has been shown to cause a transient, reversible unfolding of spore coat proteins. Heat-activated spores can then be germinated for additional time in germination buffers containing nutrient-germinants, such as L-alanine. If no nutrient-germinant is present, however, spores will return to their pre-heated, non-germinated state.

It is also known that germination can occur at ambient temperatures (near typical room temperature) without heat-activation and with a germination buffer containing nutrients, but the process takes longer (e.g. 4 hours) than with heat-activation. Additionally, non-heat-activated spores of *B. subtilis* have been known to have been germinated in non-nutrient-germinant conditions (e.g. $CaCl_2+Na_2DPA$) for an extended period of time.

It is also known to combine the use of heat activation and a nutrient-germinant to germinate spores in a two-step process in laboratory settings. The spores are first heat activated by incubating for a period of time (e.g. 30 minutes) at a temperature in the range of 65-75° C. (this specific temperature is species dependent). Then, the spores are transferred into a buffer solution that contains a nutrient-germinant, such as L-alanine. It is also known to grow bacteria in a growth chamber located near a use site by feeding pelletized nutrient material (containing sugar, yeast extract, and other nutrients that are not direct spore germinants), bacteria starter, and water into a growth chamber at a controlled temperature range of 16-40° C., and more preferably between 29-32° C., for a growth period of around 24 hours as disclosed in U.S. Pat. No. 7,081,361.

There is a need for a rapid spore activation method that will allow generation of active bacteria, such as *Bacillus* species, in a single step, using a single-serve composition at a point-of-use location where the bacteria will be discharged into a farm application. Although larger farms have the capability to supply their barns with probiotics, there is a need for smaller farms to be able to treat their barns but at an affordable cost. The single-serve system and method according to preferred embodiments of the invention will fill the gap currently seen in the industry, and will allow for a broader range of treatable farms. Accordingly, preferred embodiments of this invention provide a simple method for spore germination simultaneously with heat incubation in a single step using a single-serve nutrient-germinant concentrate combined with a spore composition in powdered or other solid form, preferably in an enclosed filter pack, for use in small farm applications (e.g. less than 10,000 chickens).

SUMMARY OF THE INVENTION

Preferred embodiments of the system and method of the invention provide a cost-effective approach to delivering an incubated (or activated) bacteria solution to small scale farm applications, such as (1) drinking water in a farm facility to improve the gut health of animals (e.g. chickens, pigs, etc.), (2) aquaculture applications (e.g. shrimp farms) to improve water quality and animal health, and (3) plants and crops through irrigation systems. The preferred embodiments of the system and method of the invention desirably include the delivery to a farm application of an incubated (or activated) bacteria solution comprising activated probiotic *Bacillus* bacteria, generated on-site using a powdered nutrient spore concentrate composition comprising nutrient-germinant ingredients and bacteria in spore form, preferably contained in a single-serving sized filter pack that is rehydrated and heat incubated in a single step.

For animal drinking water applications, an incubated (or activated) bacteria solution preferably comprises activated bacteria that are primarily still spore form bacteria in the commitment phase of germination or primarily metastable state bacteria. This activated state allows at least some of the bacteria to survive the stomach of animals that ingest them and become fully vegetative in the small intestines where they are beneficial. Although the incubated bacteria solution for animal drinking water application may comprise some vegetative state bacteria, it is preferred that the germination process be suspended before the bacteria reach the outgrowth stage by adding the incubated bacteria solution to cooler drinking water because once the bacteria go through the outgrowth period they may lose resistance associated with the spore state and not survive to reach the animal's intestines. For plant/crop and aquaculture applications, an incubated bacteria solution preferably comprises bacteria that are vegetative state bacteria, although some bacteria may still be in a metastable state and become vegetative after the application.

A nutrient-germinant composition according to one preferred embodiment of the invention comprises one or a combination of many L-amino acids (either alone, in the form of soy hydrolysate, or in combination), optionally D-glucose or D-fructose (which increases the binding affinity of L-amino acids for their cognate receptors in the spore coat), and a neutral buffer such as a phosphate buffer. According to another preferred embodiment, a nutrient-germinant composition also comprises a source of potassium ions, such as potassium chloride, monopotassium phosphate, or dipotassium phosphate. According to another preferred embodiment, the composition comprises a filler material, such as inulin or maltodextrin to increase the powder bulk of the product for efficient packaging. According to another preferred embodiment, the composition comprises an anti-caking agent to prevent clumping during storage. Preferably, the nutrient-germinant composition is in a solid form, most preferably a powdered form. The particle size for ingredients in the nutrient-germinant composition may vary depending on the specific ingredients used, for example amino acids may be in the range of around 150-300 microns and powdered soy may be in the range of around 50-100 microns.

According to another preferred embodiment, a spore composition comprises spores of one or more bacteria species, preferably *Bacillus* species, but other bacteria may also be used. Most preferably, the spore composition comprises bacterial spores that are in a dry, powder blend of 40-60% salt (table salt) and 60-40% bacteria spores. The particle sizes of the spore composition ingredients are around 1 micron for the spores and around 100-150 microns for the salt. According to another preferred embodiment, a spore composition may also comprise other excipients, such as such as sodium bicarbonate (typically at a particle size of around 50-100 microns) and/or baker's yeast.

Most preferably, a nutrient-germinant composition is combined with a spore composition to form a premixed nutrient spore composition comprising around 0.1 to 10% by weight of the spore composition, preferably between 4-8%, more preferably between 5-7%, and most preferably between 5.5-6.5% and around 90 to 99.9% by weight of the nutrient-germinant composition, preferably between 92-96%, more preferably between 93-95%, and most preferably between 93.5-94.5%. The nutrient spore composition preferably comprises bacteria amounts of around $1.0 \times 10^8$ to around $1.0 \times 10^{11}$ cfu/g of the composition, which when hydrated into an incubated bacteria solution comprises bacteria counts of around $2 \times 10^8$ to $4 \times 10^8$ cfu/ml bacteria strains and when diluted with drinking water (for animal watering applications) provide around $1.0 \times 10^3$ to $2.0 \times 10^5$ cfu/ml bacterial strains in the drinking water. The nutrient spore composition is preferably contained in a pre-measured, single use dose or filter packet for use in preferred embodiments of the systems and methods of the invention. Alternatively, separate nutrient-germinant and spore compositions may be used that are combined at the point-of-use. When separate, the compositions are preferably in pre-measured, single use dose or filter packets for use in preferred embodiments of the systems and methods of the invention. Unless premixed or separate is expressly referred to, references herein to a nutrient spore composition refer to either (1) a premixed nutrient-germinant composition and spore composition or to (2) separate nutrient-germinant and spore compositions.

According to other preferred embodiments, a separate nutrient-germinant composition or a premixed nutrient spore composition according to the invention is in concentrated, powdered form and is diluted to 0.01% to 10% strength by weight, more preferably 0.1 to 8% strength by weight, and most preferably 1 to 4% in water (preferably around 6-8 oz.) or another diluent at the point-of-use. The use of a concentrated formula reduces shipping, storage, and packaging costs and makes dosing of the nutrient spore composition at the point-of-use easier. Most preferably, if separate from the nutrient-germinant composition, the spore composition is also in a concentrated powder form, which is easy and fast to mix with diluent and the nutrient-germinant composition at the point-of-use. By using powdered forms of the separate spore composition and pre-mixed nutrient spore composition, the use of a preservative is not necessary.

According to another preferred embodiment of the invention, each single-use dose or filter packet preferably comprises around 1 to 10 grams of the nutrient-germinant composition and/or around 0.01 to 1 grams of the spore composition, more preferably around 3 to 5 grams of the nutrient-germinant composition and/or around 0.1 to 0.5 grams of the spore composition. Each single-use packet is rehydrated in an appropriate volume of water, most preferably 6-8 oz. per nutrient spore composition dose packet (or per pair of nutrient-germinant composition and spore composition dose packets), the mixture is then delivered to the farm application, such as by adding to the drinking water of livestock (e.g. chickens, cows, etc.). Most preferably, rehydration is with the use of heated water according to preferred incubation methods of the invention. When in filter packets, the packet may be steeped in water or water may be dripped or streamed over the filter packet as further described below. When in a non-permeable packet or container, the packet or container is opened and the pre-measured single-serve contents emptied into, or a measured amount from a bulk container is added to, the appropriate volume of water.

In another preferred embodiment, the present invention comprises an incubation method to germinate spores of *Bacillus* species using a premixed nutrient spore composition (or a separate nutrient-germinant composition and spore composition that is combined at the point-of-use to form a nutrient spore composition). The incubation method preferably comprises adding heated water to the nutrient spore composition for a period of time (an incubation period). The heated water is preferably in a range of 60-80° C., more preferably in the range of 65-75° C., and most preferably in the range of 72° C. to 75° C. and is allowed to contact the nutrient spore composition for an incubation period, preferably around 2 to 60 minutes, more preferably 5-50 minutes, and most preferably 20-40 minutes. The hot water will rapidly activate spores and form an incubated bacteria solution that is delivered to the farm application. Most preferably, a nutrient spore composition in concentrated form according to preferred embodiments of the invention are used in the incubation methods of the invention, but other nutrient-germinant compositions and spore compositions may also be used.

Preferably, the incubation method is carried out at or near the point-of-use, such as at the farm site or near the drinking water site where the incubated bacteria solution will be used or consumed. Preferred methods according to the invention may be carried out in any device that is capable of adding hot, non-pressurized water to the nutrient spore composition before or during an incubation period, but is preferably carried out in an incubation system according to preferred embodiments of the invention. Pressurized water and/or steam damages spores and therefore should not be used.

According to one preferred embodiment, an incubation system comprises a water reservoir, a first heating element configured to heat water from the water reservoir, a filter pack reservoir configured to hold a filter pack of nutrient spore composition (or a filter pack of nutrient-germinant composition and a filter pack of spore composition) and to receive the heated water, and a container to receive an incubated bacteria solution, configured similarly to the components in a drip-style coffee maker. A single use packet of nutrient spore composition (preferably according to preferred embodiments of the invention but other compositions may also be used) is emptied into a filter in the filter reservoir or, if the packet is a filter packet, the filter packet of nutrient spore composition is placed in the filter reservoir, and hot water is filtered over the nutrient spore composition to form an incubated bacteria composition that is delivered to the farm application. The hot water is preferably in a range of 60-80° C., more preferably in the range of 65-75° C., and most preferably in the range of 72° C. to 75° C. Most preferably, the water is in contact with the nutrient spore composition (either in the filter reservoir, the container for the incubated bacteria solution, or a combination thereof) for an incubation period of 2 to 60 minutes, more preferably 2 to 10 minutes or less, depending on the farm application, to form the incubated bacteria solution. Most preferably, an incubation system is configured to dispense an amount of heated water to the filter reservoir, such as 6-8 oz., that is sufficient to rehydrate the single-use dose of nutrient spore composition and allow germination of the bacteria to begin.

The preferred embodiments of the invention allow for rapid germination of spores of *Bacillus* species at a farm point-of-use. The incubated bacteria solution discharged from the incubation system and method can be administered directly into the drinking water reservoir of animals or into the irrigation systems of crops or an aquaculture growing pond. Most preferably, in order to achieve a beneficial quantity of bacteria delivered per animal, 6-8 oz. of incubated spore solution may be added to every 500-1000 L of drinking water. For agriculture applications, one 6-8 oz. dose (containing approx. $6 \times 10^{10}$ CFU (total)) may be added to the amount of water needed to irrigate 1-2 acres of vegetation, with the amount of irrigation water varying depending on local rainfall and the type of crop being grown. Most preferably one 6-8 oz. dose would be added to the needed amount of water every watering cycle to treat 1-2 acres of crops. For aquaculture, one 6-8 oz. dose may be added to every 300,000-800,000 L pond (approx. 79,000-210,000 gallons), which will result in approximately 200 CFU/mL for a 300,000 L pond to approximately 75 CFU/mL for a 800,000 L pond., with additional doses being added for larger ponds.

BRIEF DESCRIPTION OF THE DRAWINGS

The system and method of the invention are further described and explained in relation to the following drawing:

FIG. 1 shows microscope images of slides using a nutrient spore composition and incubation method according to a preferred embodiment of the invention compared to control slides.

DESCRIPTION OF THE PREFERRED EMBODIMENTS

According to one preferred embodiment, an incubated bacteria solution is generated on-site from a single-serve nutrient spore composition, preferably using a drip-style water incubation system and incubation method as described below, and the incubated bacteria solution is batch fed into a drinking water reservoir or other farm application.

A nutrient spore composition according to one preferred embodiment of the invention comprises (1) spores, (2) one or more L-amino acids, (3) optionally D-glucose (which increases the binding affinity of L-amino acids for their cognate receptors in the spore coat and is optional), (4) optionally D-Fructose (optional, depending on bacteria species), (5) a biological buffer to provide the proper pH for spore germination (such as HEPES sodium salt, a phosphate buffer, or a Tris buffer), and (6) an optional source of potassium ions (such as KCl, or monopotassium phosphate or dipotassium phosphate). When monopotassium and/or dipotassium phosphate are used as a source of potassium ions, they can also act as a buffer, making it unnecessary to add a separate buffer. Ingredients (2)-(6) may also be part of a separate nutrient-germinant composition that is mixed with a spore composition or separate packets of each used together at a point-of-use. In another preferred embodiment, the nutrient spore composition comprises both D-glucose and D-fructose. The use of D-glucose, D-fructose, a combination of D-glucose and D-fructose, and a potassium ion source are dependent on the species of bacteria as will be understood by those of ordinary skill in the art. According to another preferred embodiment, no D-glucose or D-fructose are used in a nutrient germinant composition or nutrient spore composition. According to another preferred embodiment, a nutrient spore composition further comprises one or more filler materials/bulking agents and/or one or more anticaking agents. According to another preferred embodiment, the composition is in a concentrated form, most preferably as a powder, and is hydrated and heated at the point-of-use. Preferred L-amino acids include L-alanine, L-asparagine, L-valine, and L-cysteine. In a further embodiment of the concentrate composition, L-amino acids can be provided as a hydrolysate of soy protein.

When in a preferred solid, most preferably powered form, a nutrient spore composition preferably comprises around (1) 0.1 to 10% by weight of a spore composition, most preferably around 5-6%; (2) one or more of the above mentioned L-amino acids in the range of 8-20%, more preferably 9.5-17%, and most preferably 10-16% each; (3) D-glucose (optional) and/or D-fructose (optional) in the range of 15-27%, more preferably 19-23%, and most preferably 20-22.5% each; (4) a source of potassium (optional, but preferably KCl) in the range of 6.6-11%, more preferably 7.9-9.7%, and most preferably 8.4-9.2%; and (5) buffers comprising (a) monosodium phosphate in a range of 0.9-1.5%, more preferably 1.1-1.4%, and most preferably 1.15-1.3% (b) disodium phosphate in a range of 2.8-4.8%, more preferably 3.4-4.2%, and most preferably 3.6-4%, (c) Tris base in a range of 4.3-7.1%, more preferably 5.1-6.3%, and most preferably 5.4-6%; (d) HEPES buffer in a range of 8.4-14.1%, more preferably 10.1-12.4%, and most preferably 10.7-11.8%, (e) monopotassium phosphate in a range of 8.4-14%, more preferably 10.1-12.3%, and most preferably 10.6-11.7% (as total amounts for use as both a buffer and a source of potassium, if needed or desired), (f) dipotassium phosphate in a range of 3.5-5.8%, more preferably 4.1-5.1%, and most preferably 4.4-4.8% (as total amounts for use as both a buffer and a source of potassium, if needed or desired), or (g) a combination thereof. According to another preferred embodiment, monosodium phosphate and disodium phosphate are used together as the one or more buffers. Although use of a source of potassium is optional, when monopotassium and/or dipotassium phosphate are used as buffers they also act as a potassium source making it unnecessary to use any other source of potassium, such as potassium chloride, which may be omitted. The amounts of these ingredients are important aspects of preferred embodiments of the invention because higher concentrations would render some ingredients insoluble and unable to activate spores and lower concentrations would be ineffective at germinating spores. These percentages are by weight of the solid/powdered nutrient spore composition.

The nutrient spore composition may also include a filler or bulking agent to increase the bulk of the powder. The bulking agent would compose preferably 58.5-98%, more preferably 70.6-86.2% and most preferably 74.5-82.3% of the composition. Bulking agents may include hydrolyzed soy, corn flour, rice flour, microcrystalline cellulose, or other known bulking agents. In order to prevent clumping or hardening, the nutrient spore composition may also include an anticaking agent in the ranges of 0.2-3.8%, more preferably 0.3-4.5%, and most preferably 0.5-2.1%. These percentages are by weight of the solid/powdered nutrient-spore composition.

According to another preferred embodiment, a powered nutrient spore composition comprises around (1) 0.1 to 10% by weight of a spore composition, most preferably around 5-7%; (2) 8-20%, more preferably 9.5-17%, and most preferably 10-16% of one or more L-amino acids, most preferably at least L-alanine; (3) 59 to 98%, more preferably 67-90%, and most preferably 74-82% hydrolyzed soy; (4) monosodium phosphate in a range of 0.9-1.5%; and (5) disodium phosphate in a range of 2.8-4.8%, more preferably 3.4-4.2%, and most preferably 3.6-4%. The spores in this embodiment preferably comprise *Bacillus subtilis, Bacillus licheniformis, Bacillus pumilus, Bacillus amyloliquefaciens, Bacillus simplex,* or a combination thereof. If necessary, this embodiment may include a source of potassium, and D-glucose, or D-fructose. These percentages are by weight of the solid/powdered nutrient spore composition.

Once the nutrient spore composition is added to an amount of water to form a hydrated bacteria solution in concentrated form, which becomes the incubated bacteria solution at the end of the incubation period, it preferably comprises around (1) $2\times10^{11}$ to $4\times10^{11}$ CFU/L bacteria spores, more preferably $2.4\times10^{11}$ to $3.4\times10^{11}$ CFU/L; (2) one or more of the above mentioned L-amino acids in the range of 1.5-4.5 g/L, more preferably 2-3.6 g/L, and most preferably 2.1-3.5 g/L each; (3) D-glucose (optional) and/or D-fructose (optional) in the range of 3-6 g/L, more preferably 4-5 g/L, and most preferably 4.3-4.7 g/L each; (4) optionally a source of potassium, such as KCl in the range of 1-3 g/L, more preferably 1.5-2.5 g/L, and most preferably 1.7-2.1 g/L; and (5) buffers comprising (a) monosodium phosphate in a range of 0.1-0.4 g/L, more preferably 0.2-0.3 g/L, and most preferably 0.25-0.28 g/L, (b) disodium phosphate in a range of 0.5-1.0 g/L, more preferably 0.7-0.9 g/L, and most preferably 0.75-0.85 g/L, (c) Tris base in a range of 0.75-1.5 g/L, more preferably 1-1.4 g/L, and most preferably 1.2-1.3 g/L, (d) HEPES buffer in a range of 1.5-3 g/L, more preferably 2-2.6 g/L, and most preferably 2.3-2.5 g/L, (e) monopotassium phosphate in a range of 1.5-3 g/L, more preferably 2-2.5 g/L, and most preferably 2.2-2.5 g/L, (f) dipotassium phosphate in a range of 0.5-1.5 g/L, more preferably 0.75-1.25 g/L, and most preferably 0.85-1.1 g/L, or (g) a combination thereof According to another preferred embodiment, monosodium phosphate and disodium phosphate are used together as the one or more buffers. Although use of a source of potassium is optional, when monopotassium and/or dipotassium phosphate are used as buffers they also act as a potassium source making it unnecessary to use any other source of potassium, such as potassium chloride, which may be omitted. The amounts of these ingredients are important aspects of the invention because higher concentrations would render some ingredients insoluble and unable to activate spores and lower concentrations would be ineffective at germinating spores.

The hydrated bacteria solution or composition (or incubated bacteria solution) also preferably comprises around 2-5 g/L, more preferably 3-4.5 g/L and most preferably 3.5-4 g/L total of the one or more fillers or bulking agents as described herein. The composition also preferably comprises 0.03-1.3 g/L total, more preferably in a range of around 0.1-1 g/L total, and most preferably in a range of around 0.2-0.625 g/L total of the one or more anticaking agents as described herein. When a hydrated composition is made using a filter pack or separate filter with a system and method according to preferred embodiments of the invention, the fillers/bulking agents and/or anticaking agents may remain in the spent filter pack or separate filter (depending on ingredient particle size and filter pore size) and therefore may not be present in a hydrated composition/incubated bacteria solution or may be present in smaller quantities than indicated above.

According to another preferred embodiment, once the nutrient spore composition is added to an amount of water to form a hydrated bacteria solution in concentrated form, which becomes the incubated bacteria solution at the end of the incubation period, it preferably comprises around (1) $2\times10^{11}$ to $4\times10^{11}$ CFU/L bacteria spores, more preferably $2.4\times10^{11}$ to $3.4\times10^{11}$ CFU/L; (2) 1.5-4.5 g/L, more preferably 2-3.6 g/L, and most preferably 2.1-3.5 g/L of one or more L-amino acids, most preferably at least L-alanine; (3) 12 to 21 g/L, more preferably 14 to 19 g/L, and most preferably 15 to 17 g/L hydrolyzed soy; (4) 0.1-0.4 g/L, more preferably 0.2-0.3 g/L, and most preferably 0.25-0.28 g/L monosodium phosphate; and (5) 0.5-1.0 g/L, more preferably 0.7-0.9 g/L, and most preferably 0.75-0.85 g/L disodium phosphate. The spores in this embodiment preferably comprise *Bacillus subtilis, Bacillus licheniformis, Bacillus pumilus, Bacillus amyloliquefaciens, Bacillus simplex* or a combination thereof. If necessary, this embodiment may include a source of potassium, and D-glucose, or D-fructose.

According to another preferred embodiment, a spore composition comprises spores of one or more bacteria species, preferably *Bacillus* species, but other bacteria may also be used. Most preferably, the spore composition comprises bacterial spores in a dry, powder blend of 40-60% salt (table salt) and 60-40% bacteria spores, the percentages by weight of the spore composition.

Most preferably, a nutrient-germinant composition is combined with a spore composition to form a premixed nutrient spore composition comprising around 0.1 to 10% by weight of the spore composition, most preferably around 5-6% and around 90 to 99.9% by weight of the nutrient-germinant composition, most preferably around 95-94%. A separate nutrient-germinant composition preferably comprises the preferred ingredients identified above for a nutrient spore composition (excluding the spores or spore composition) in amounts proportionally adjusted from those listed above. A nutrient spore composition preferably comprises bacteria in an amount of around $1.0\times10^8$ to around $1.0\times10^{11}$ cfu/g of the composition, which when diluted with drinking water (for animal watering applications) provide around $1.0\times10^3$ to $2.0\times10^5$ cfu/ml bacterial strains in the drinking water. The nutrient spore composition is preferably contained in a pre-measured, single-use dose or filter packet for use in preferred embodiments of the systems and methods of the invention. Most preferably, a nutrient spore concentrate composition, according to some embodiments of the invention, is in powdered form and is hydrated and diluted to a working solution in water or any other appropriate diluent, preferably at the point-of-use. The dilution is preferably in a range from 0.1-10% of the concentrate and the balance water by weight. The amount of water used is specific to the formula in order to achieve the preferred concentrations of nutrient components. Larger quantities of water may reduce the activation potential of the nutrient spore composition.

According to one preferred embodiment, a separate spore composition or a nutrient spore composition preferably comprises one or more species of *Bacillus* in spore form. The preferred *Bacillus* spores include the following species: *Bacillus licheniformis, Bacillus subtilis, Bacillus amyloliquefaciens, Bacillus polymyxa, Bacillus thuringiensis, Bacillus megaterium, Bacillus coagulans, Bacillus lentus, Bacillus clausii, Bacillus circulans, Bacillus firmus, Bacillus lactis, Bacillus laterosporus, Bacillus laevolacticus, Bacillus polymyxa, Bacillus pumilus, Bacillus simplex, Bacillus sphaericus,* and *Bacillus toyonensis*. Other *Bacillus* spore species may also be used as will be understood by those of ordinary skill in the art. Most preferably, the composition comprises 1 to 12 *Bacillus* species, more preferably 2 to 3 *Bacillus* species. For poultry applications, the composition preferably comprises 2 species of *Bacillus*, most preferably *Bacillus subtilis* and *Bacillus licheniformis* (preferably in a 1:2 to 2:1 ratio, depending on the specific strains uses) (any ratio between these ratios, such 1.3:1.7, 1.6:1.4, may also be used). For porcine or bovine applications, similar ratios may be used and the *Bacillus* may include any combination of *Bacillus subtilis, Bacillus licheniformis, Bacillus pumilus,*

*Bacillus toyonensis, Bacillus coagulans, Bacillus lentus, Bacillus amyloliquefaciens, Bacillus megaterium,* or *Bacillus simplex*. For aquaculture applications, the composition preferably comprises 2 species of *Bacillus*, most preferably *Bacillus licheniformis* and *Bacillus pumilus* (preferably in 1:2 ratio, but any ratio between 1:2 to 2:1, such 1.3:1.7, 1.6:1.4, may also be used). And for crop applications, the composition preferably comprises up to 8 different *Bacillus* species, most preferably a combination of *Bacillus subtilis, Bacillus licheniformis, Bacillus pumilus, Bacillus toyonensis, Bacillus amyloliquefaciens, Bacillus megaterium, Bacillus simplex*, and/or *Bacillus thuringiensis*.

In another preferred embodiment, a separate spore composition or a nutrient spore composition for use as a probiotic comprises one or more *Bacillus* strains that are probiotic in nature in that they aid in the breakdown of nutrients in the digestive tract of the consumer or in the soil of a crop. The strains preferably produce one or more of the following enzymes: proteases to hydrolyze proteins, amylases to hydrolyze starches and other carbohydrates, lipases to hydrolyze fats, glycosidases to assist in the hydrolysis of glycosidic bonds in complex sugars and to assist in degradation of cellulose, cellulases to degrade cellulose to glucose, esterase which is a lipase-like enzyme, and xylanases that degrade xylan, a polysaccharide found in plant cell walls. *Bacillus* strains that produce these enzymes are well known in the art and include *Bacillus* species such as *subtilis, licheniformis,* and *pumilus*. In another preferred embodiment, the spores contained in the compositions degrade prebiotic ingredients such as inulin and raffinose. These prebiotics are known to those in the art as being "nutrients" that select for (i.e. induce the growth of) beneficial, probiotic bacteria in the gut.

In another preferred embodiment, a nutrient spore composition may further comprise one or more bulking agents or filler materials to increase the bulk of the composition. The filler material may be inert (such as one that does not add to the efficacy of the composition) or may be functional (such as one that does add to the efficacy of the composition). Inert fillers may include maltodextrin, soluble starch, flour, and other known fillers. Functional fillers may include the soluble fiber inulin (which serves as a prebiotic and may increase the functionality of probiotics in the gut), powder soy sauce, tamari soy, yeast extract, or hydrolyzed soy protein powder (different from the soy hydrosolate that can be used for an L-amino acid). Regardless of the type of bulking agent, the composition preferably comprises around 2-5 g/L, more preferably 3-4.5 g/L and most preferably 3.5-4 g/L total of the one or more fillers or bulking agents.

In another embodiment, a nutrient spore composition may further comprise an anticaking agent to prevent clumping and binding during storage. Ingredients used in preferred embodiments of the composition (such as powdered soy sauce) may be sensitive to humidity and may absorb water during storage, causing the powdered composition to harden or clump. Anticaking agents are anhydrous and absorb excess moisture to prevent this hardening and clumping. They may be added to the composition or used to coat humidity-sensitive particles of certain ingredients to repel moisture. Most preferably, the anticaking agents are generally regarded as safe (GRAS) and may include compounds such as: calcium chloride, calcium phosphate, silicates (calcium and magnesium), methylcellulose, cornstarch, microcrystalline cellulose, lecithin, maltodextrin, sodium aluminosilicate, sodium chloride, sodium phosphate, starch, and powdered yeast. When in a preferred powdered form, the composition preferably comprises one or more anticaking agents preferably in a range of around 0.03-1.3 g/L total, more preferably in a range of around 0.1-1 g/L total, and most preferably in a range of around 0.2-0.625 g/L total of the one or more anticaking agents.

Most preferably, nutrient spore compositions are contained in a pouch or packet containing enough composition to generate a single dose of bacteria solution when an appropriate amount of water is added. Preferably, each single-use pouch or packet comprises around 1 to 10 grams of the nutrient-germinant composition and/or around 0.01 to 1 grams of the spore composition, more preferably around 3 to 5 grams of the nutrient-germinant composition and/or around 0.1 to 0.5 grams of the spore composition. Each single-use pouch or packet is rehydrated in an appropriate volume of water to achieve preferred concentration ranges for the ingredients in the hydrated bacteria solution as described above to provide around $2 \times 10^8$ to $4 \times 10^8$ CFU/mL, which will be further diluted when added to water in the farm application (e.g. animal drinking water or an aquaculture growing pond) to preferred application concentration ranges of $6 \times 10^4$ to $2 \times 10^5$ CFU/mL. For the packet size amounts referenced above, the appropriate amount of water is preferably between 2-16 oz., more preferably 6-8 oz. water, per nutrient spore composition dose packet (or per pair of separate nutrient-germinant composition and spore composition dose packets). The dose of bacteria solution is then delivered to the farm application, such as by adding to the drinking water of livestock (e.g. chickens, cows, etc.). Most preferably, the dose of bacteria solution is incubated to form an incubated bacteria solution using preferred systems and methods of the invention prior to being delivered to the farm application. Each 6-8 oz. dose of bacteria solution (or incubated bacteria solution) comprises around $2 \times 10^8$ to $4 \times 10^8$ CFU/mL is preferably sufficient to treat 500-1000 L of animal drinking water or 20,000 to 200,000 gallons of an aquaculture growing pond or 1-2 acres of crops. Multiple single-use packets of nutrient spore composition may be used to treat larger volumes of water or larger acreage in farm applications, as needed. Most preferably the bacteria solution (or incubated bacteria solution) is added to the farm application on a periodic basis, such as once per day to once per week, as needed.

An incubation method according to a preferred embodiment comprises adding heated water to a nutrient spore composition (preferably according to an embodiment of the invention) to germinate spores of *Bacillus* species for a period of time (an incubation period). The heated water is preferably in a range of 60-80° C., more preferably in the range of 65-75° C., and most preferably in the range of 72° C. to 75° C. The temperature ranges herein include each individual temperature within the range and any subrange within such ranges, including subranges that overlap from one preferred range to a more preferred range. The heated water will rapidly activate spores and, after the incubation period, will form an incubated bacteria solution that is delivered to the farm application. Most preferably, the spores in the nutrient spore composition are not heat treated or pre-heated prior to adding the water. Most preferably, the heated water and nutrient spore composition are combined by dripping or streaming the hot water over the nutrient spore composition without using pressurized water or steam or the nutrient spore composition is steeped in the heated water.

One preferred incubation device for use in the systems and methods of preferred embodiments of the invention comprises an on-site, small-scale water drip system, such as a coffee maker or hot water dispenser. Most preferably, an incubation system comprises a water reservoir, a first heating element configured to heat water from the water reservoir, a filter pack reservoir configured to hold a filter pack of nutrient spore composition (or a filter into which loose powder nutrient spore composition is added) and to receive the heated water, and a container (or third reservoir) to hold an incubated bacteria solution. The container (or third reservoir) is preferably removable from the incubation device (like a coffee pot in a drip coffee maker) to allow easy transport of the incubated bacteria solution to a nearby discharge point (e.g. a drinking water trough). The filter reservoir is preferably disposed above the removable container to allow gravity flow of bacteria solution from the filter reservoir to the container through one or more apertures in a bottom of the filter reservoir. An incubation system also preferably comprises a siphon tube configured to thermosiphon hot water from the water reservoir to deliver it to the filter pack reservoir. Alternatively, the water reservoir may also be disposed above the filter reservoir to allow dispensing of heated water by gravity feed using a valve to release the water once heated or a small dispensing aperture or tube that limits the flow rate of water from the water reservoir to the filter reservoir to allow time for the water to be heated. If a valve is used, it may be connected to a controller to automatically open and close the valve at the appropriate time when the incubation system turned on or activated. Alternatively, a separate water reservoir may be omitted and water added directly to the filter reservoir, which is then heated by the heating element.

The heating element may also be configured, or a second heating element may be provided, to heat the removable container to maintain the temperature of the bacteria solution in the above ranges, particularly over longer incubation periods or when ambient temperatures are substantially lower than the heated temperature range. Most preferably, the filter reservoir is also removable from the incubation device to allow easy disposal of the filter or remaining filter material from a filter pack of nutrient spore composition after the water is dispensed into the removable container (or third reservoir) without having to touch the filter/filter pack, which may still be hot.

Alternatively, when a filter pack of nutrient spore composition (or filter packs of separate compositions) is used, a filter reservoir may be omitted and the filter pack may be placed directly into the removable container according to another preferred embodiment. In that embodiment, the removable container preferably comprises a removable or openable lid configured to allow the filter pack to be inserted into the container and to allow the incubated bacteria solution to be poured or dispensed from the container while retaining the spent filter pack in the container so that the spent filter pack does not get dispensed to the end use application (e.g. a water trough) and may be disposed of after the bacteria solution is dispensed.

As an additional alternative, a nutrient spore composition (or separate compositions) in loose powdered form may be directly added to the container and hot water added to the container, in which case the filter reservoir and use of a filter may be omitted. Although the use of a pre-packaged filter pack aids in having a pre-measured amount of nutrient-spore composition, a bulk powder that is measured on-site may also be used. If a bulk powder is used, it may be necessary to mix or stir the ingredients once water is added as some ingredients are slower to solubilize.

A filter pack containing a pre-measured amount of nutrient spore composition, preferably according to preferred embodiments of the invention but other compositions may also be used, is added to the filter reservoir. Alternatively, nutrient spore composition is a free, loose powder that is added to a separate filter (such as a standard coffee filter) in the filter reservoir (or the filter reservoir may be made of metal, ceramic, or plastic mesh material to act as a filter, without needing a separate filter) or directly to the removable container to which hot water is added to generate the incubated bacteria solution. When loose powder is used, most preferably, the powder is in a pre-measured dose packet that is opened and added to the filter reservoir or removable container, but may also be in a larger, bulk container with a scoop or other measuring device that allows a pre-determined amount of powder (equivalent for one dose of bacteria solution) to be the added to the filter reservoir. A filter used with the preferred system and method of the invention may be a standard coffee filter with a pore size of approx. 5-100 microns, or a packet or a pouch made of the same material, or a tea-style bag made of fiber or nylon. Whatever material is used as the filter material, it is most preferable that the pore size is greater than 1 micron to allow passage of *Bacillus* spores through the filter material and into a container for the incubated bacteria solution. Fillers, bulking agents, and/or anticaking agents may remain in the filter after the water has filtered through. The filter, filter packet, or other packet or pouch material is discarded after generating the incubated bacteria solution.

The nutrient spore composition, or specific ingredients in the composition, may be sensitive to moisture and experience clumping at humidity levels during shipping or storage over 50 to 60%. It is preferred to store the nutrient spore composition (or separate nutrient-germinant and spore compositions) in climate controlled environments prior to packing in a filter pack or pod. Once packaged, the filter packs or pods are tolerant up to about 80% humidity. However, it is preferred to include a desiccant with bulk containers of the nutrient spore composition (or separate compositions) and with bulk containers of the filter packs or pods containing the composition(s), to protect against higher humidity conditions that may be encountered during storage at an end-use farming facility, particularly in coastal, tropical, and subtropical climates. Alternatively, or in addition to desiccants in the containers, the nutrient spore composition (or specific ingredients used therein) preferably comprises one or more anticaking agents to prevent clumping.

Heated water, preferably in a range of 60-80° C., more preferably in the range of 65-75° C., and most preferably in the range of 72° C. to 75° C., is delivered to the filter reservoir to contact the filter pack or packs or the loose powder composition (in a filter in the filter reservoir or that has been added directly to the removable container when no filter reservoir is used). Most preferably a small stream of water or dripping water is added to the filter reservoir by gravity feed. To avoid damaging the spores, it is preferred that pressurized water flow and/or steam not be used to rehydrate the nutrient spore composition. Most preferably, the placement of the filter packs or separate filter in the filter reservoir allows heated water to fill or partially fill the filter reservoir before being discharged through the bottom aperture(s) to allow greater contact between the water and filter pack compositions to dissolve the powder, allowing the nutrient spore composition ingredients in solution to exit the filter before the water/solution is discharged to the removable container below the filter reservoir. Most preferably, an incubation system is configured to dispense an amount of heated water to the filter reservoir, preferably 6-8 oz. that is sufficient to rehydrate the pre-measured dose of the nutrient spore composition and allow germination of the bacteria to begin. Most preferably, the spores in the nutrient spore composition are not heat treated or pre-heated prior to adding the water to the filter pack or filter reservoir.

According to another preferred embodiment, an incubation system further comprises a second heating element disposed under or in contact with the container, to keep the container warm as the solution is dispensed from the filter reservoir. The first and second heating elements may be separate or may be the same heating element in contact with multiple parts of the system to provide heat. The container is preferably heated to maintain the solution at a temperature in the range of a range of 60-80° C., more preferably in the range of 65-75° C., and most preferably in the range of 72° C. to 75° C. during the full incubation period to form an incubated bacteria solution that is then dispensed to the farm application. Most preferably, an incubation system also comprises a thermostat or a thermometer or similar measuring device coupled with a controller that can determine the temperature of the water and/or the bacteria solution in the removable container and compare it to the desired temperature range and/or a duration of heating time, so the heating element(s) can be deactivated when the desired temperature is reached and/or at the end of an incubation period, to avoid overheating the water and/or the removable container. These may also be used to reactivate or turn the heating element(s) back on if the temperature drops below the temperature range and the incubation period has not ended. Additionally, a simple timer may be used to deactivate the heating element(s) after a pre-determined amount of time that corresponds to sufficient heating time to raise the temperature of the amount of water to the desired temperature and/or the end of an incubation period, as will be understood by those of ordinary skill in the art.

According to another preferred embodiment, an incubation system includes a timer to indicate when an incubation period is over, which allows a user to know when the incubated bacteria solution is ready to be applied to the farm application. Most preferably, the system comprises different timer settings for different incubation periods, depending on the farm application in which the incubated bacterial solution will be used. The timer may be connected to a switch or controller to turn off the heating element (particularly if the removable container is heated) at the end of the incubation period. Additionally, the system may also comprise one or more audible or visual (such as a flashing light) alarm signals to indicate the end of the incubation period and to indicate the end of one or more predetermined periods of time (such as two minutes and five minutes) after the end of the incubation period if the container of incubated bacteria solution is not removed from the incubation system. It is preferred to apply the incubated bacteria solution to the farm application soon after the end of the incubation period to ensure that viable bacteria survive to the desired beneficial destination. For example, with animal applications, it is important to discharge the incubated bacteria solution to the drinking water quickly after the incubation period in order to suspend the germination process after the bacteria are activated but before they become fully vegetative, because vegetative bacteria are not likely to survive to the animal's intestines where they are beneficial. Even for plant/crop or aquaculture applications, where the germination process can continue until the bacteria in the incubated bacteria solution are fully vegetative before dispensing to the farm application, waiting too long before application can result in the bacteria running out of food source and dying off before they have had a chance to be of use in the soil or pond, for example.

An incubation system also preferably comprises a plug to receive power from a standard power outlet or a battery pack to provide power to the heating element(s) and optionally to any controller, timer, valve, or alarm if included in the incubation system.

In another preferred embodiment, the nutrient spore composition is in a single-serve filter packet or pouch that is placed on a tray or other container onto which a pre-measured amount of hot water drips over it releasing the spores and nutrient components into a removable container to form an incubated bacteria solution. In another preferred embodiment, a single-serve pod, packet, or pouch is placed in a container with a measured amount of hot water and allowed to steep or soak for an incubation period, similar to steeped tea, to dissolve the nutrient spore composition in the water to form the incubated bacteria solution. Most preferably, the pod, packet, or pouch of nutrient spore composition is submerged in the water while steeping or soaking. The water in these embodiments is also heated to a temperature in the range of 60-80° C., more preferably in the range of 65-75° C., and most preferably in the range of 72° C. to 75° C.

Using incubation systems and methods according to preferred embodiments of the invention, an incubated bacteria solution is formed by contacting the nutrient spore composition with the hot water for an incubation period of 2 minutes to 60 minutes. When a drip-coffee maker style incubation system is used, or other device that allows water to drip over a filter packet of nutrient-spore composition or otherwise be slowly added to a nutrient spore composition, the incubation period begins once all of the water has been dispensed over the filter pack to contact the nutrient spore composition. Most preferably, all of the water will be added to the filter reservoir or dripped over the tray or other container holding the filter packet of nutrient spore composition within 60 to 180 seconds and filtering will be complete (dispensed to the removable container for the incubated solution) in about 1.5 to 5 minutes, more preferably around 2 to 2.5 minutes. When steeping the nutrient germinant composition in the removable container or adding loose powder and water directly to the removable container, preferably water is slowly dripped or streamed (without pressure) over the filter packet or loose powder in the same time periods described for the filter reservoir. Alternatively, water may be added to the removable container first and then the filter pack or loose powder of nutrient spore composition may be added to the water. The germination process for the incubated bacteria solution will continue until all of the bacteria are vegetative or the solution is cooled down, such as by adding the solution to cooler animal drinking water, which is typically at a temperature of 15 to 32° C.

For an animal probiotic application, the incubation period is preferably between around 2 minutes to 5 minutes. After the incubation period, the incubated bacteria solution is preferably quickly added to added to a drinking water reservoir (up to 1000 L), preferably in less than 5 minutes from the end of the incubation period, more preferably less than 3 minutes. The addition of the mixture to the cooler drinking water suspends the spores in an activated state and does not allow them to proceed to the outgrowth stage. Allowing the bacteria to remain in the hot water of the removable container any longer, such as 5 minutes after the end of the 2-5 minute incubation period, before distribution into cooler drinking water will allow the spores to go through outgrowth period in which they may lose resistance associated with the spore state and not survive to reach the animal's intestines. Preferably at least 85%, more preferably at least 90%, and most preferably at least 95% of the bacteria in the incubated bacteria solution for adding to drinking water is in an activated state, but not yet in the outgrowth stage or vegetative.

For a plant or crop probiotic application or an aquaculture application, the incubation period is preferably between around 5 minutes to 60 minutes. The extended incubation period allows for full germination of the probiotic spores to a vegetative state so that they may begin working immediately after application to the plant/crop or aquaculture pond. After the extended incubation period, the incubated bacteria solution may be applied directly to a plant or added to an irrigation system or an aquaculture pond. Once vegetative, the water temperatures typically found in irrigation systems and aquaculture ponds will not negatively impact the bacteria. The incubated bacteria solution may also be applied to the plant/crop or aquaculture pond before the bacteria is fully vegetative.

After incubation using a preferred composition and method, each batch of incubated or activated bacteria solution comprises around $1\times10^6$-$1\times10^9$ cfu/mL of spores, more preferably around $1\times10^7$-$8\times10^8$, and most preferably around $2\times10^8$-$6\times10^8$ cfu/mL. Most preferably, sufficient quantities of incubated spore solution are added to the water to provide an effective amount of bacteria based on the dilution. In this context, "effective amount" can refer to the amount of bacteria and/or nutrient composition that can be effective to improve performance of an animal or crop after administration. Multiple single-serve nutrient spore "batches" may be needed to provide larger quantities of activated bacteria solution to the water to achieve the desired effective amount for the animal or crop. For example, an effective amount for chickens is around $10^6$ to $10^8$ CFU/day per chicken, more preferably around $10^7$ to $5\times10^7$ CFU/day Although it is usually not problematic to overfeed the bacteria solution to the animals, it is generally unnecessary to feed more than these amounts.

A nutrient spore composition according to preferred embodiments of the invention was tested according to preferred methods of the invention. The composition, method, and results are described below.

EXAMPLE 1—To germinate spores, a nutrient spore composition was prepared according to a preferred embodiment of the invention. The nutrient spore composition comprised L-alanine (2.225 g), monosodium phosphate (0.25 g), disodium phosphate (0.8 g), hydrolyzed soy (3.9 g), and probiotic *Bacillus* spores (1.25 g) in a sealed, porous filter pod. The pod was added to one side of the brew tray (a filter reservoir) of an off-the-shelf single-serve drip coffee maker (Cuisinart 2 Cup Coffee Maker) and approx. 8 oz. of water was added to the water reservoir. Power was applied to the unit and hot water (approx. 72° C.) was drip-dispensed onto the pod. A cup was used for collection of the heated, hydrated mixture. It took about 2.5 minutes for all water to dispense into the cup. After the mixture sat in the cup for an incubation period of 5 minutes (a preferred incubation period for a drinking water point-of-use, with the five minute time period beginning after all of the water was dispensed to the cup), an incubated bacteria solution was formed. For testing purposes, 1 mL of the heated, incubated bacteria solution mixture was incubated on a pre-heated heat block at 42° C. for 1 hour. This additional heating step was used to get the spores through activation and right up to the outgrowth step in order to be able to count germination/activation efficiency for comparison to a room temperature example. Depending on the end use application, such an additional heating period may or may not be used as part of an incubation period. After the one hour heating, the sample was centrifuged for 2 minutes to collect the spores. For comparison, a negative control reaction was prepared with the same nutrient spore composition, but the pod was rehydrated by placing the pod in room temperature water (approx. 23° C.). After 5 minutes, 1 mL of the negative control composition was incubated at room temperature (approx. 23° C.) for 1 hour after which the sample was centrifuged for 2 minutes to collect the spores.

Spores from each reaction were observed using phase contrast microscopy. Slides were prepared using standard procedures. Spores were viewed on an Olympus BX41 microscope (100× oil emersion objective) and imaged using an Olympus UC30 camera controlled by the cellSens Dimension software package.

FIG. 1 shows representative images from these tests. Images in panel A represent spores that had been incubated using a preferred nutrient spore composition coupled with a preferred incubation system and method according to the invention. The darker spots show completely germinated spores that have started outgrowth, the lighter spots show non-germinated spores. Images in panel B represents spores incubated with a preferred nutrient spore composition at ambient temperature (23° C.) without using a preferred incubation system and method according to the invention. As can be seen in FIG. 1, the "A" images show significantly more germinated spores (dark spots) than the "B" images. Spores incubated with a nutrient spore composition according to a preferred embodiment invention in combination with a preferred incubation system and method (Example 1, FIG. 1A) resulted in almost all spores germinating, whereas almost no spores were germinated in the control group (Example 1, FIG. 1B) incubated at room temperature with a nutrient spore composition according to a preferred embodiment of the invention, but without using an incubation system and method according to a preferred embodiment of the invention. The small percentage of spores in the control group that did germinate are believed to be due to stochastic events that result in spontaneous germination. This example demonstrates that spore germination is significantly increased when a nutrient-germinant composition and incubation method according to preferred embodiments of the invention are used together.

Additional tests were run using a Keurig® coffee maker with a pressurized water stream. The spores in the incubated spore solution from the Keurig appeared normal (or similar) to the spores tested with a drip-style coffee maker; however, the pressurized stream negatively impacted the viability of the spores. The composition of Example 1 yields approx. $1\times10^9$ cfu/mL when it was steeped with a drip coffee maker. When the composition used in Example 1 was put through a Keurig® coffee maker, the counts were approx. $1\times10^7$ cfu/mL, which is a significant reduction. Accordingly, it is preferred to not use a Keurig® type coffee maker or any other pressurized water stream for providing water to hydrate nutrient-spore compositions according to the invention.

Any ingredient, apparatus or system features or components, or method steps of a preferred embodiment herein may be used with any other ingredients, features, components or steps of other embodiments even if not specifically described with respect to that embodiment, unless such is explicitly excluded herein. Any ingredient or amount of an ingredient, apparatus or system features or components, or method steps described as included or excluded with any particular preferred embodiment herein may similarly be included or excluded with any other preferred embodiment herein even if not specifically described with such embodiment. All numerical values for amounts of ingredients, ratios, temperatures, and incubation periods, herein described as a range specifically include any individual value or ratio within such ranges and any and all subset combinations within ranges, including subsets that overlap from one preferred range to a more preferred range and even if the specific subset of the range is not specifically described herein. Those of ordinary skill in the art will also appreciate upon reading this specification and the description of preferred embodiments herein that modifications and alterations to the device may be made within the scope of the invention and it is intended that the scope of the invention disclosed herein be limited only by the broadest interpretation of the appended claims to which the inventors are legally entitled.

We claim:

1. A method of incubating bacteria spores at a point-of-use comprising the following steps:
   providing 1 to 10 grams of a nutrient spore composition in powdered form, the nutrient spore composition comprising one or more *Bacillus* species in spore form;
   heating 6 to 8 ounces of water to a temperature in a temperature range of 60° C. to 75° C. to produce a heated water;
   streaming or dripping the heated water over the nutrient spore composition without using pressurized flow of the heated water to form a hydrated bacteria solution; and
   incubating the hydrated bacteria solution for an incubation period of around 2 to 60 minutes to form a single dose of an incubated bacteria solution.

2. The method of claim 1 wherein the nutrient spore composition comprises 90-99.9% by weight of a nutrient-germinant composition and 0.1-10% by weight of a spore composition;
   wherein the nutrient-germinant composition is in powdered form and comprises: (1) L-alanine, (2) a phosphate buffer or Tris base or combination thereof, and (3) optionally a source of potassium ions;
   wherein the spore composition is in powdered form and comprises (1) salt and (2) the one or more *Bacillus* species consists of *Bacillus subtilis, Bacillus licheniformis*, or *Bacillus pumilus* in spore form.

3. The method of claim 1 wherein the nutrient spore composition comprises:
   0.1-10% of a spore composition in powdered form, the spore composition comprising the one or more *Bacillus* species in spore form;
   around 8-20% of one or more L-amino acids;
   one or more buffers comprising around: (a) 0.9-1.5% monosodium phosphate, (b) 2.8-4.8% disodium phosphate, (c) 4.3-7.1% Tris base, (d) 8.4-14.1% HEPES, (e) 8.4-14% monopotassium phosphate, or (f) 3.5-5.8% dipotassium phosphate; and
   optionally around 6.6-11% of a source of potassium;
   wherein the percentages are by weight.

4. The method of claim 3 wherein the one or more buffers comprises the monopotassium phosphate or the dipotassium phosphate or both and the nutrient spore composition does not include any potassium chloride.

5. The method of claim 3 wherein the one or more *Bacillus* species in spore form are not heat treated or heat activated prior to the streaming or dripping step.

6. The method of claim 3 wherein the nutrient spore composition does not include any industrial preservative or germination inhibitor.

7. The method of claim 3 wherein the temperature range is 65° C. to 72° C.

8. The method of claim 3 wherein the temperature range is 72° C. to 75° C.

9. The method of claim 3 wherein the nutrient spore composition further comprises hydrolyzed soy, wherein the one or more L-amino acids comprises L-alanine, and wherein the one or more buffers comprises the monosodium phosphate and the disodium phosphate.

10. The method of claim 1 wherein the incubated bacteria solution comprises:
    around 1.5-4.5 g/L of one or more L-amino acids comprising L-alanine;
    one or more bulking materials, filler materials, or anti-caking materials; and
    one or more buffers comprising around (a) 0.1-0.4 g/L monosodium phosphate, (b) 0.5-1.0 g/L disodium phosphate, (c) 0.75-1.5 g/L Tris base, (d) 1.5-3 g/L HEPES, (e) 1.5-3 g/L monopotassium phosphate, or (f) 0.5-1.5 g/L dipotassium phosphate; and
    optionally around 1-3 g/L of a potassium source.

11. The method of claim 10 wherein the one or more buffers are the monosodium phosphate and the disodium phosphate.

12. The method of claim 10 wherein the potassium source is potassium chloride.

13. The method of claim 10 wherein the streaming or dripping step comprises allowing the heated water to stream or drip under gravity flow.

14. The method of claim 10 wherein the nutrient spore composition is contained in a filter pouch within a container, wherein the streaming or dripping step comprises streaming or dripping the heated water over the filter pouch within the container and the incubating step comprises allowing the filter pouch to steep in the heated water.

15. The method of claim 10 wherein the point-of-use is animal drinking water and further comprising adding the single dose of the incubated bacteria solution to the animal drinking water;
    wherein the incubation period is around 2 to 5 minutes; and
    wherein at least 85% of the one or more *Bacillus* species in the incubated bacteria solution is in an activated state but has not reached an outgrowth stage when it is added to the animal drinking water.

16. The method of claim 1 further comprising adding the single dose to the point-of-use and wherein the point-of-use is animal drinking water, an aquaculture pond, or soil around a plant.

17. A method of incubating bacteria spores at a point-of-use comprising the following steps:
    providing a nutrient spore composition in powdered form, the nutrient spore composition comprising one or more *Bacillus* species in spore form;
    heating water to a temperature in a range of 60° C. to 75° C. to produce a heated water;
    streaming or dripping the heated water over the nutrient spore composition without using pressurized flow of the heated water to form a hydrated bacteria solution;
    incubating the hydrated bacteria solution for an incubation period of around 2 to 60 minutes to form a single dose of an incubated bacteria solution;
    adding the single dose to the point-of-use and wherein the point-of-use is animal drinking water, an aquaculture pond, or soil around a plant; and
    repeating the providing, heating, streaming or dripping, incubating, and adding steps to form a desired number of additional single doses of the incubated bacteria solution, wherein each additional single dose is added to the point-of-use once every 12 to 24 hours.

18. The method of claim 16 wherein the incubated bacteria solution comprises the one or more *Bacillus* species as activated, metastable state spores when the point-of-use is the animal drinking water.

19. A method of incubating bacteria spores at a point-of-use comprising the following steps:
providing a nutrient spore composition in powdered form, the nutrient spore composition comprising one or more *Bacillus* species in spore form;
heating water to a temperature in a range of around 60° C. to 80° C. to produce a heated water;
streaming or dripping the heated water over the nutrient spore composition without using pressurized flow of the heated water to form a hydrated bacteria solution;
incubating the hydrated bacteria solution for an incubation period of around 2 to 60 minutes to form a single dose of an incubated bacteria solution;
suspending germination of the one or more *Bacillus* species at an activated, metastable state by adding the incubated bacteria solution to animal drinking water having a temperature in a range of 15° C. to 32° C.

20. The method of claim 1 further comprising heating the hydrated bacteria solution during the incubation period to maintain the temperature in the temperature range.

21. The method of claim 17 wherein the one or more *Bacillus* species in spore form does not include *Bacillus coagulans*.

22. The method of claim 1 wherein the one or more *Bacillus* species in spore form does not include *Bacillus coagulans*.

23. The method of claim 17 wherein the one or more *Bacillus* species in spore form consists of *Bacillus subtilis*, *Bacillus licheniformis*, or *Bacillus pumilus*.

24. The method of claim 19 wherein the one or more *Bacillus* species in spore form consists of *Bacillus subtilis*, *Bacillus licheniformis*, *Bacillus pumilus*, *Bacillus amyloliquefaciens*, or *Bacillus simplex*.

25. The method of claim 16 wherein the incubated bacteria solution comprises the one or more *Bacillus* species as vegetative bacteria when the point-of-use is the soil around a plant or the aquaculture pond.

* * * * *